(12) United States Patent
Weissman et al.

(10) Patent No.: US 11,453,625 B1
(45) Date of Patent: Sep. 27, 2022

(54) PROCESS OF PRODUCING ETHYLENE

(71) Applicant: PRECISION COMBUSTION INC, North Haven, CT (US)

(72) Inventors: Jeffrey G Weissman, Guilford, CT (US); Codruta Maria Zoican-Loebick, North Haven, CT (US)

(73) Assignee: PRECISION COMBUSTION INC., North Haven, CT (US)

( * ) Notice: Subject to any disclaimer, the term of this patent is extended or adjusted under 35 U.S.C. 154(b) by 0 days.

(21) Appl. No.: 17/243,065

(22) Filed: Apr. 28, 2021

Related U.S. Application Data

(60) Provisional application No. 63/023,304, filed on May 12, 2020.

(51) Int. Cl.
| | | |
|---|---|---|
| *C07C 5/327* | (2006.01) | |
| *B01J 20/34* | (2006.01) | |
| *C07C 7/13* | (2006.01) | |

(52) U.S. Cl.
CPC ........... *C07C 5/327* (2013.01); *B01J 20/3425* (2013.01); *C07C 7/13* (2013.01)

(58) Field of Classification Search
CPC ......... C07C 5/327; C07C 7/13; B01J 20/3425
See application file for complete search history.

(56) References Cited

U.S. PATENT DOCUMENTS

| | | |
|---|---|---|
| 5,051,241 A | 9/1991 | Pfefferle |
| 6,156,444 A | 12/2000 | Smith |
| 6,328,936 B1 | 12/2001 | Roychoudhury |
| 7,141,092 B1 | 11/2006 | Roychoudhury |
| 10,220,347 B2 | 3/2019 | Vijayakumari |
| 10,239,013 B2 | 3/2019 | Vijayakumari |
| 2019/0284483 A1 | 9/2019 | Spicer |

FOREIGN PATENT DOCUMENTS

| | | |
|---|---|---|
| WO | WO2002024614 A1 | 3/2002 |
| WO | WO2015031370 A1 | 3/2015 |
| WO | WO2018118306 A1 | 6/2018 |

OTHER PUBLICATIONS

L. Mei, et al., "Adsorption performance of MIL-100 (Fe) for separation of olefin-paiaffin mixtures," Journal of the Taiwan Institute of Chemical Engineers, 70 (2017), 74-78.
J. Bachman et al., "M2 (m-dobdc) (M=Mn, Fe, Co, Ni) Metal—Organic Frameworks as Highly Selective, High Capacity Adsorbents for Olefin / Paraffin Separations," J. Am. Chem. Soc., 139 (2017), 15363-15370.

(Continued)

*Primary Examiner* — Thuan D Dang
(74) *Attorney, Agent, or Firm* — Marie Zuckerman; Andrew D. Gathy

(57) ABSTRACT

A process of producing ethylene involving steam cracking ethane to produce a steam cracker product stream containing ethylene; cooling and drying the steam cracker product stream; contacting the cooled and dried steam cracker product stream with a MOF sorbent capable of adsorbing ethylene from the product stream, and desorbing the ethylene from the MOF sorbent using an ethylene sweep gas. The process replaces complex and energy intensive fractionation steps of the prior art with a selective adsorption step for separating ethylene from the steam cracker product stream. An energy efficient ethylene sorbent regeneration method and related apparatus systems are also disclosed.

20 Claims, 2 Drawing Sheets

(56) References Cited

OTHER PUBLICATIONS

T. Hahnel, et al., "Adsorptive separation of C2/C3/C4—hydrocarbons on a flexible Cu-MOF: The influence of temperature, chain length and bonding character," Microporous and Mesoporous Materials, 224 (2016), 392-399.

X. Cui, et al.,"Pore chemistry and size control in hybrid porous materials for acetylene capture from ethylene," Science, 353 (2016), Issue 6295, 141-144.

Y. Zhang, et al., "Highly Selective Adsorption of Ethylene over Ethane in a MOF Featuring a Combination of Open Metal Sites and the A-Complexation," The Royal Society of Chemistry, Chem. Commun., 51 (2015), 2714-2417; DOI: 10.1039/c0xx0000x.

Y. He et al., "A new MOF-5 homologue for selective separation of methane from C2 hydrocarbons at room temperature," APL Materials 2, 124102 (2014).

Z. Herm, E. Bloch, J. Long, "Hydrocarbon Separations in Metal-Organic Frameworks," Chemistry of Materials, 26 (2014), 323-338.

E. Bloch, et al., "Hydrocarbon Separations in a Metal-Organic Framework with Open Iron (II) Coordination Sites," Science, 335 (2012), 1606-1610.

E. Worrell, D. Phylipsen, D. Einstein, N. Martin, "Energy Use and Energy Intensity of the U.S. Chemical Industry," Lawrence Berkeley National Laboratory, LBNL-44314 (2000), 1-40.

D. B. Manley, "Thermodynamically Efficient Distillation: Ethylene Recovery," www.semanticscholar.org; [web.mst.edu] (1999).

PROCESS OF PRODUCING ETHYLENE

CROSS-REFERENCE TO RELATED APPLICATIONS

This application claims benefit of U.S. provisional application No. 63/023,304, filed May 12, 2020.

GOVERNMENT RIGHTS

This invention was made with support from the U.S. government under Contract No. DOE-SC0018619, sponsored by the Department of Energy. The U.S. Government holds certain rights in this invention.

FIELD OF THE INVENTION

This invention pertains to an improved process of producing ethylene starting from ethane. This invention also pertains to an apparatus system for producing ethylene and for separating ethylene from a steam cracker product stream.

BACKGROUND OF THE INVENTION

Present day industrial methods of converting ethane into ethylene involve an energy intensive, multi-step process. At the start, an ethane feed is preheated to about 650° C.; then the preheated ethane feed is mixed with steam and cracked in a steam cracker using radiant heat at a temperature of about 850° C. The product gas from the steam cracker is rapidly cooled to a temperature of about 400° C. to quench the cracking reaction. Heat recuperated from the cooling step is used to convert water into high pressure steam. Water injection is used to cool the product gas to further decrease temperature to about 40° C., thereby generating a gas fraction and a liquid condensate rich in aromatics. Various liquid fractions are extracted from the liquid condensate. The gas fraction is subjected to low temperature, high pressure fractional distillation through a series of columns including a demethanizer, deethanizer, depropanizer and debutanizer, thereby producing overhead fractions of C1 (methane) C2's (ethane, ethylene, acetylene), C3's (propane, propylene, methylacetylene, propadiene), and C4's (butane, butylene), respectively, as overhead gaseous products and ultimately a C5+ bottoms stream. The C2's overhead stream is partially hydrogenated to convert the acetylene to ethylene and then sent to a splitter to separate the ethylene from ethane. The C3's overhead stream is partially hydrogenated to convert the methylacetylene and propadiene to propylene and then sent to a splitter to separate propylene from propane. Process steam from the cracking step is used to provide power to various compressors for these fractionations. The methane overhead C1 stream, which additionally comprises hydrogen, is treated cryogenically to temperatures as low as −162° C. resulting in a purified methane stream; this final step being vital to the overall economic viability of the process.

The aforementioned present day process of producing ethylene is highly energy intensive and requires a complex apparatus system. In terms of energy consumption, ethane steam cracking consumes roughly 4.8 gigajoules per metric tonne of ethylene produced (4.8 GJ/t C2H4). Compression through various compressors requires roughly 3.5 GJ/t C2H4; while the fractionation process itself consumes roughly 4.2 GJ/t C2H4, resulting in a total energy requirement of about 12.5 GJ/t C2H4.

Ethylene is employed worldwide as a feedstock for production of core chemicals including, for example, ethylbenzene, ethylenedichloride, ethylene oxide and ethylene glycol, as well as for production of polymers and copolymers including, for example, polyethylene, polystyrene, poly(vinylchloride), poly(ethylene glycol), poly(vinyl alcohol) and poly(ethylene terephthalate). Global demand for ethylene reached 143 million tonnes in 2015. Clearly, the art would benefit from discovery of a simpler and more energy efficient industrial process and apparatus system for producing ethylene.

SUMMARY OF THE INVENTION

In one aspect, this invention provides for a novel and improved process of producing ethylene, comprising:
(a) contacting an ethane feedstream and steam in a steam cracker under process conditions sufficient to prepare a steam cracker product stream comprising ethylene;
(b) cooling the steam cracker product stream under process conditions sufficient to obtain a cooled steam cracker product stream comprising ethylene and substantially free of water and liquid hydrocarbon condensates;
(c) contacting the cooled steam cracker product stream from step (b) with an ethylene sorbent comprising a substrate having supported thereon a metal-organic framework compound capable of selectively adsorbing ethylene, under adsorption conditions sufficient to remove the ethylene from the cooled stream cracker product stream; and
(d) when the ethylene sorbent is at least partially saturated with ethylene, stopping the flow of the cooled steam cracker product stream; and contacting the at least partially saturated ethylene sorbent with a flow of sweep ethylene under desorption conditions sufficient to regenerate the ethylene sorbent and recover a purified ethylene product stream comprising the sweep ethylene and desorbed ethylene.

In another aspect, this invention provides for a novel and improved apparatus system for producing ethylene, comprising:
(a) a steam cracker configured to convert a mixture of ethane and steam into a steam cracker product stream comprising ethylene;
(b) a cooling module fluidly coupled to the steam cracker, the cooling module having disposed thereon a cooling module inlet configured to receive the steam cracker product stream and a cooling module outlet configured to output a cooled steam cracker product stream comprising ethylene and substantially free of water and liquid hydrocarbon condensates;
(c) at least one ethylene adsorption unit fluidly coupled to the cooling module outlet and having disposed therein an ethylene sorbent comprising a substrate having supported thereon a metal-organic framework compound capable of selectively adsorbing ethylene;
the at least one ethylene adsorption unit (c) further configured for an adsorption cycle with (c)(i) an adsorption cycle inlet configured to receive the cooled steam cracker product stream from (b) and to contact said cooled steam cracker product stream with the ethylene sorbent so as to remove ethylene, and (c)(ii) an adsorption cycle outlet configured to output a steam cracker product stream substantially free of ethylene; and the at least one ethylene adsorption unit (c) further configured for a desorption cycle with (c)(iii) a desorption cycle inlet configured to receive an ethylene sweep stream and to contact said ethylene sweep stream with an at least partially saturated ethylene sorbent; and (c)(iv) a desorption cycle outlet configured to output a purified ethylene product stream comprising the sweep ethylene and desorbed ethylene.

In another aspect, this invention provides for a method of separating a chemical product stream comprising ethylene, the method comprising:
(a) contacting a chemical product stream comprising ethylene with an ethylene sorbent comprising a substrate having supported thereon a metal-organic framework compound capable of selectively adsorbing ethylene, under adsorption conditions sufficient to remove the ethylene and to produce a chemical product stream substantially free of ethylene; and
(b) when the ethylene sorbent is at least partially saturated with ethylene, stopping the flow of the chemical product stream, and contacting the ethylene sorbent with a flow of sweep ethylene under desorption conditions sufficient to regenerate the ethylene sorbent and to produce a purified ethylene product stream comprising the sweep ethylene and desorbed ethylene.

In another aspect, this invention provides for an apparatus for separating a chemical product stream comprising ethylene, the apparatus comprising:
at least one ethylene adsorption unit having disposed therein an ethylene sorbent comprising a substrate having supported thereon a metal-organic framework compound capable of selectively adsorbing ethylene;
the ethylene adsorption unit further configured for an adsorption cycle with: (i) an adsorption cycle inlet configured to receive the chemical product stream comprising ethylene and to contact said stream with the ethylene sorbent so as to remove ethylene, and with (ii) an adsorption cycle outlet configured to output a chemical product stream substantially free of ethylene; and
the at least one ethylene adsorption unit being further configured for a desorption cycle with: (iii) a desorption cycle inlet configured to receive an ethylene sweep stream and to contact said ethylene sweep stream with an at least partially saturated ethylene sorbent; and (iv) a desorption cycle outlet configured to output a purified ethylene product stream comprising the sweep ethylene and desorbed ethylene.

In another aspect, this invention provides for a process of regenerating an ethylene sorbent comprising contacting a flow of sweep ethylene with an ethylene sorbent comprising a substrate having supported thereon a metal-organic framework compound capable of adsorbing ethylene, the sorbent being at least partially saturated with adsorbed ethylene, the contacting occurring under desorption conditions sufficient to regenerate the ethylene sorbent and recover a purified ethylene product stream comprising the sweep ethylene and desorbed ethylene.

The process and apparatus of this invention provide for a more streamlined, energy efficient, and cost effective method of producing ethylene when compared with the conventional industrial process of producing ethylene. At the start, the process of this invention completely eliminates the costly and energy intensive fractionation and cryogenic separation steps of the conventional process. Instead, the process of this invention advantageously replaces those fractionation and cryogenic separation steps with an adsorption process step, one that utilizes a metal-organic framework (MOF) sorbent capable of separating ethylene from the steam cracker product stream, post-removal of higher hydrocarbons and water.

The desorption step of this invention, employed to regenerate the at least partially saturated ethylene sorbent, contrasts with prior art desorption processes. Typically, the prior art process employs a sweep gas, also referred to as a purge gas or flush gas, (e.g., nitrogen, air, carbon dioxide or steam) having a different composition from the adsorbed compound. The prior art process disadvantageously produces a diluted stream of desorbed compound that requires separation from the sweep gas and subsequent concentration. In contrast, the process of this invention beneficially employs a sweep gas of ethylene to desorb the adsorbed ethylene and regenerate the MOF sorbent, thereby producing a purified ethylene stream uncontaminated with any dissimilar sweep gas or diluent. Using ethylene as a sweep gas eliminates any requirement to separate the product ethylene from a sweep gas of different chemical composition. In our invention, the ethylene sweep gas is sourced simply from a vessel whose ethylene originates in the ethylene production process itself. As a further advantage, in contrast to present day industrial ethylene processes employing several compressors during the fractionation and cryogenic stages, the process of this invention employs only one comparatively low pressure compressor functioning to partially or totally preheat the ethylene sweep gas used in the final desorption step.

In view of the above, as a further technical advantage, the ethylene separation method of this invention by itself is applicable to any chemical product stream comprising ethylene. Such chemical product streams can be derived, for example, from oxidative coupling of methane, or non-oxidative coupling of methane, or oxidative dehydrogenation of ethane, or non-oxidative dehydrogenation of ethane.

DRAWINGS

DETAILED DESCRIPTION OF THE INVENTION

Figure 1:
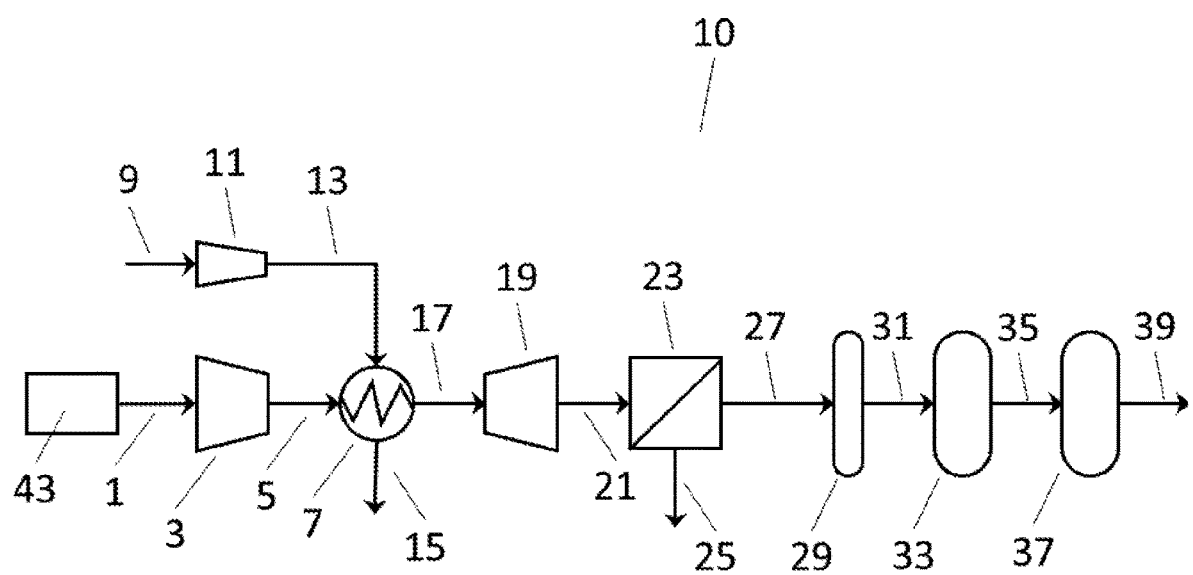
FIG. 1 illustrates an embodiment of the process of this invention from the ethane cracker reactor stage through the adsorption stage.

In one illustrative embodiment, this invention provides for a process of producing ethylene comprising:
(a) contacting an ethane feedstream and steam in a steam cracker under process conditions sufficient to prepare a steam cracker product stream comprising ethylene;
(b) cooling the steam cracker product stream under process conditions sufficient to obtain a cooled steam cracker product stream substantially free of water and liquid hydrocarbon condensates;
(c) contacting the cooled steam cracker product stream with a water sorbent so as to obtain a dried steam cracker product stream;
(d) contacting the dried steam cracker product stream with an ethylene sorbent comprising a mesh substrate having an ultra-short-channel-length and having supported thereon a metal-organic framework compound capable of selectively adsorbing ethylene, the contacting occurring under adsorption conditions sufficient to remove the ethylene from the dried stream cracker product stream;

(e) when the ethylene sorbent is at least partially saturated with ethylene, stopping the flow of the dried steam cracker product stream; and thereafter contacting the at least partially saturated ethylene sorbent with a flow of sweep ethylene under desorption conditions sufficient to regenerate the ethylene sorbent and to recover a purified ethylene product stream comprising the sweep ethylene and desorbed ethylene.

In another related embodiment, the purified ethylene product stream consists essentially of the sweep ethylene and the ethylene desorbed from the ethylene sorbent.

In another illustrative embodiment, after step (e) of the aforementioned process, steps (a) through (e) are repeated for a selected period of time.

In another illustrative embodiment, process step (b) comprises (b)(i) cooling the steam cracker product stream to a temperature between about 20° C. and about 60° C.; (b)(ii) passing the cooled steam cracker product stream through a compressor; and (b)(iii) passing a resulting compressed steam cracker product stream into a hot side of a heat exchanger; whilst passing water, air, or other fluid(s) through a cold side of the heat exchanger. Thereafter, (b)(iv) the steam cracker product stream is passed through an expander, so as to produce a tertiary cooled steam cracker product stream having a reduced water and liquid hydrocarbons content and having a temperature between about 0° C. and about 10° C. Concomitantly, a water condensate is produced; and the water condensate as well as liquid hydrocarbons are removed in a condenser/separator vat. The tertiary steam cracker product stream is then passed into step (c) of this invention, as detailed hereinabove.

In another illustrative embodiment, the flow of sweep ethylene utilized in step (e) is preheated by passing an unheated sweep ethylene stream through a cold side of a heat exchanger; whilst passing the purified ethylene product stream through a compressor and then into a hot side of the heat exchanger, so as to transfer heat from the purified ethylene product stream to the unheated sweep ethylene stream, thereby producing the preheated flow of sweep ethylene. Additional heating can be provided to further increase the temperature of the preheated flow of sweep ethylene.

In another illustrative embodiment, this invention provides for an apparatus system for producing ethylene, comprising;
(a) a steam cracker configured to convert a mixture of ethane and steam into a steam cracker product stream;
(b) a cooling module fluidly coupled to the steam cracker, and comprising a cooling module inlet configured to receive the steam cracker product stream and a cooling module outlet configured to output a cooled steam cracker product stream substantially free of water and liquid hydrocarbon condensates;
(c) a water adsorption unit having disposed therein a water sorbent capable of selectively adsorbing water; the water adsorption unit being further configured for an adsorption cycle with: (c)(i) a water adsorption cycle inlet configured to receive the cooled steam cracker product stream and further configured to contact said product stream with the water sorbent, and (c)(ii) a water adsorption cycle outlet configured to output a dried steam cracker product stream;
the water adsorption unit being further configured for a desorption cycle with (c)(iii) a water desorption cycle inlet configured to receive a first sweep gas, and contact said first sweep gas with an at least partially saturated water sorbent, and (c)(iv) a water desorption cycle outlet configured to exhaust a first sweep gas product stream containing the first sweep gas and desorbed water; and
(d) at least one ethylene adsorption unit fluidly coupled to the water adsorption unit and having disposed therein an ethylene sorbent comprising a mesh substrate having an ultra-short-channel-length and having supported thereon a metal-organic framework compound capable of selectively adsorbing ethylene;
the at least one ethylene adsorption unit (d) further configured for an adsorption cycle with: (d)(i) an ethylene adsorption cycle inlet configured to receive the dried steam cracker product stream and to contact said product stream with the ethylene sorbent, and with (d)(ii) an ethylene adsorption cycle outlet configured to exhaust a steam cracker product stream substantially free of ethylene; and
the at least one ethylene adsorption unit (d) further configured for a desorption cycle with (d)(iii) an ethylene desorption cycle inlet configured to receive an ethylene sweep stream ("second sweep stream") and to contact said ethylene sweep stream with an at least partially saturated ethylene sorbent; and (d)(iv) an ethylene desorption cycle outlet configured to output a purified ethylene product stream comprising the sweep ethylene and desorbed ethylene.

In another illustrative embodiment, when under operative conditions the first sweep gas comprises ethane, then the first sweep gas product stream containing ethane and desorbed water is fluidly coupled to an inlet to the steam cracker.

In yet another illustrative embodiment, the purified ethylene product stream exiting outlet (d)(iv) is fluidly coupled to a hot side of a heat exchanger; while an unheated ethylene sweep feed is fluidly coupled to a cold side of the heat exchanger; and further the heat exchanger is configured to transfer heat from the purified ethylene product stream to the unheated ethylene sweep feed so as to produce a preheated ethylene sweep stream that is input to ethylene desorption cycle inlet (d)(iii). Additional heaters can be provided to further increase the temperature of the preheated flow of sweep ethylene.

In another illustrative embodiment, this invention provides for a process of regenerating an ethylene sorbent comprising contacting a flow of sweep ethylene with an ethylene sorbent comprising a mesh substrate having an ultra-short-channel-length and having supported thereon a metal-organic framework compound capable of selectively adsorbing ethylene, the ethylene sorbent being at least partially saturated with adsorbed ethylene; the contacting occurring under desorption conditions sufficient to regenerate the ethylene sorbent and to recover a purified ethylene product stream comprising the sweep ethylene and desorbed ethylene.

In another illustrative embodiment, the substrate employed in the ethylene sorbent comprises a MICROLITH® brand mesh substrate having an ultra-short-channel-length ranging from about 25 microns (25 μm) to about 500 μm.

Figure 2:
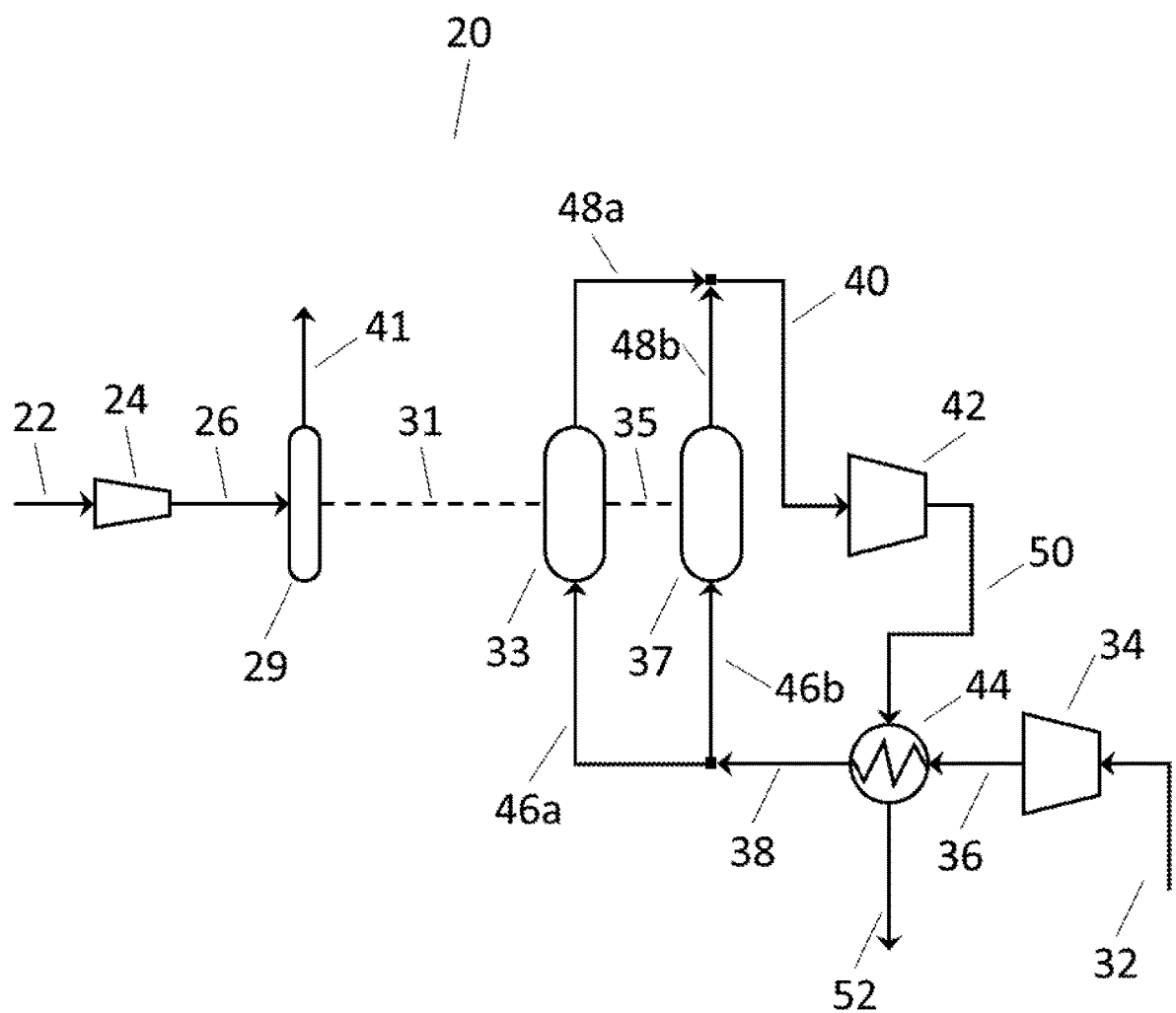
FIG. 2 illustrates an embodiment of the process of this invention at the desorption stage.

The process and apparatus system of this invention will be further clarified and better understood by a consideration of the attached drawings. Reference is made to FIGS. 1 and 2, which collectively illustrate the process and apparatus of this invention and, respectively, embodiments of the adsorption cycle 10 and desorption cycle 20. With respect to FIG. 1, a conventional steam cracker is configured to contact ethane and steam to produce a steam cracker product stream, which is cooled conventionally. These process steps and apparatus units are simply represented by unit 43 on FIG. 1. An ethylene steam cracker (ESC) product stream 1, already quenched and cooled by conventional means to a temperature of between about 40-50° C. and already having a reduced concentration of higher boiling hydrocarbons, is fed into a cooling module, collectively comprising fluidly coupled compressor 3, heat exchanger 7, expander 19, and condenser 23 of FIG. 1. As such, steam cracker product stream 1 is compressed in ESC compressor 3. The compressed ESC stream 5 is passed into a hot side of heat exchanger 7. Air stream 9 is compressed in air blower 11 and passed as air stream 13 into a cold side of heat exchanger 7, emerging as hotter air stream 15. A cooler ESC product stream 17 is passed into expander 19, emerging as expanded and cooler ESC product stream 21 having a temperature between about 0° C. and about 10° C. The product stream 21 is sent to condenser unit 23 from which water condensate stream 25 is removed as well as residual hydrocarbon condensate. A cool and substantially water-free gaseous ESC product stream 27 is taken from condenser unit 23 and passed into fluidly coupled water sorbent unit 29, at which point ESC product stream 27 contacts the water sorbent disposed therein removing any residual water. The dried ESC product stream 31 emerging from water sorbent unit 29 is sent to a fluidly coupled first ethylene sorbent unit 33, where the dried ESC stream contacts a metal-organic framework sorbent that selectively adsorbs ethylene from the stream passing there through. ESC stream 35 depleted in ethylene emerges from the first ethylene sorbent unit 33 and is sent to second ethylene sorbent unit 37, where the ethylene sorbent therein selectively adsorbs any ethylene remaining in the ESC stream 35. A tail gas stream 39, comprising ethane essentially free of ethylene, is recovered from ethylene sorbent unit 37.

When the tail gas stream 39 exhibits an unacceptable break-through of water or ethylene or a combination thereof, or gas stream 31 exhibits an unacceptable break-through of water, indicating at least partial saturation of at least one of the sorbent units 29, 33 and 37, the adsorption process is shut down and the adsorption units are regenerated. As illustrated in FIG. 2, regeneration of water sorbent unit 29 is simply effected by passing a first sweep stream 22, for example, an inert non-reactive gas (He, Ar), air or an essentially pure ethane feed stream, through blower 24 to obtain blower sweep stream 26, which is fed to the water sorbent unit 29 where it is contacted with the water sorbent disposed therein, thereby producing a first sweep product stream 41 containing the first sweep gas and a quantity of desorbed water. Typically, this water desorption process is conducted at ambient pressure and at a temperature greater than about 45° C., and preferably, ranging from about 50° C. to about 110° C. In one preferred embodiment, the first sweep stream 26 is ethane; and thus first product sweep stream 41 consists essentially of ethane and desorbed water, which is cycled to the ethane steam cracker (ESC) 43 and consists of at least part of the total ethane feed to the ethane steam cracker.

An embodiment of the desorption cycle of the ethylene sorbent is also illustrated in FIG. 2. Here, an unheated ethylene sweep stream 32 derived from any compressed ethylene tank is passed into expander 34, emerging as expanded ethylene sweep stream 36, which is passed into a cold side of ethylene sweep heat exchanger 44. A heated ethylene sweep gas stream 38 emerges from the heat exchanger 44 and is passed as heated ethylene sweep streams 46a and 46b into the ethylene sorbent units 33 and 37, respectively, where adsorbed ethylene is thermally desorbed and the units are regenerated. A purified ethylene product stream is recovered as streams 48a and 48b, combined into purified ethylene stream 40, which is passed into compressor 42 and from thence as stream 50 into a hot side of sweep gas heat exchanger 44, emerging as purified ethylene product stream 52, comprising the sweep ethylene and the desorbed ethylene, this stream being sent to a bank of compressed ethylene product tanks. Note that streams 31 and 35 as illustrated in FIG. 2 are employed during the adsorption cycle and not employed during the desorption cycle.

The first stage of the process of this invention utilizes any conventional steam cracker reactor and steam cracking process conditions known for converting ethane into ethylene and also for converting other hydrocarbons including gasoils and naphthas into ethylene. Since these reactors and processes are well known in the art, reference is made to the following illustrative patent: International patent publication WO 2018/118306, incorporated herein by reference; and to the following illustrative literature: D. B. Manley, "Process Designs for Ethylene Recovery", 5th World Congress of Chemical Engineering, AIChE, Volume 4, 317-322, July (1996), and E. Worrell, D. Phylipsen, D. Einstein, N. Martin, Lawrence Livermore Berkeley Laboratory LLBL DE-AC03-765F00098, April, 2000. For ethane cracking generally, the hydrocarbon feed to the steam cracker comprises from about 50 to about 100 mole percent ethane. Propane may be present as a lessor component, for example, in a concentration from about 5 mole percent to less than 50 mole percent. Under steam cracking conditions, the cracking of ethane and propane results in production of a steam cracker gaseous product stream comprising a mixture of methane, ethylene, propylene, hydrogen, acetylene, methylacetylene and propadiene, as well as any unconverted ethane and propane. As well, quantities of C4, C5, and C6 hydrocarbons are likely to occur in the product stream; but as these are higher molecular weight than ethane and propane, their concentrations are lower. Ethane crackers typically operate at a temperature ranging from about 750° C. to about 950° C., more preferably, about 850° C. A residence time of the ethane feed stream in the steam cracker is on the order of milliseconds.

The gaseous steam cracker product stream is rapidly cooled to quench any further reactions. At the start, cooling follows a conventional process of heat exchange to reduce temperature to a range from about 350° C. to about 450° C., during which time a high pressure steam is produced for recycle to the steam cracker. Then water is injected into the gaseous steam cracker product stream to decrease its temperature further to about 40° C. to 50° C., thereby forming a condensate rich in hydrocarbons.

From this stage onward, rather than proceeding with the costly conventional fractionation steps of the prior art, the cooled steam cracker product stream is treated in accordance with the process of this invention. Thus, after the aforementioned conventional cooling and removal of hydrocarbon condensates, the gaseous steam cracker product stream is subjected to a refrigeration cycle to remove substantially all of its water content. The process steps include, as noted hereinabove, (b)(ii) compressing the cooled stream cracker product stream in a compressor; and (b)(iii) passing a resulting compressed stream cracker product stream into a hot side of a heat exchanger; whilst passing air, water, or other suitable fluid through a cold side of the heat exchanger. Thereafter, (b)(iv) the steam cracker product stream is expanded by passage through an expander, so as to produce a cooler steam cracker product stream having a reduced water content and having a temperature between about 0° C. and about 10° C. At this lower temperature, substantially all of the bulk water condenses and is separated out as water stream 25 in a liquid knockout condenser 23 as illustrated in FIG. 1. Additionally, any hydrocarbons with boiling points greater than about 0° C. and less than about 10° C., such as C5 and C6 hydrocarbons, will also condense. Optionally, this condensate product 25 can be recycled into the steam cracking unit 43. The overhead 27 from the condenser 23 comprises a cooled gaseous steam cracker product stream (FIG. 1/27) that is rich in lower boiling hydrocarbons, namely methane, ethane, ethylene, propane, propylene and C4 hydrocarbons, which fraction is fed into the water sorbent unit 29, or alternatively, directly into the first ethylene sorbent unit 33.

In one embodiment, after cooling and removal of bulk water and higher boiling condensates, the cooled steam cracker product stream 27 is subjected to the additional drying step to remove residual water; however, this additional drying step is optional and particularly useful when the metal-organic framework (MOF) compound of the ethylene sorbent is water sensitive. Conversely, if the MOF is not water sensitive, this drying step may be unnecessary and eliminated. This optional drying step involves contacting the cooled steam cracker product stream with a water sorbent under conditions sufficient to remove any residual water remaining in the product stream 27. The water sorbent comprises any sorbent capable of adsorbing water from a gaseous mixture, suitable non-limiting examples of which include molecular sieves and zeolites, including for example aluminosilicates, aluminas, silicas including silica gels, and also metal-organic framework (MOF) sorbents. Among suitable molecular sieves, one finds molecular sieves X, Y, 13X and MS5A, which are commercially available. In one preferred embodiment, molecular sieve 13X is employed. The cooled ethylene product stream is contacted with the water sorbent at a temperature ranging from about 0° C. to about 10° C. and a pressure ranging from about 0.9 bar to about 1.1 bar. Generally, the thusly-dried water content of the dried steam cracker product stream 31 is less than about 1 percent, preferably, less than about 0.5 percent, and more preferably, less than about 0.01 percent, by volume.

When the water sorbent is saturated or partially saturated, leading to an unacceptable quantity of water breaking into the dried steam cracker product stream 31, the flow of cooled steam cracker product stream 27 is stopped and the water sorbent is regenerated. Generally, a sorbent is regenerated by thermal or vacuum desorption or by depressurization of a high-pressure sorbent bed. The sorbent bed is heated in one embodiment by electrical resistance heating of bed elements, or in another embodiment by conductive heating by applying heat to an exterior of the bed, or in another preferred embodiment by convective heating by passing a suitable heated fluid through the bed. In yet another embodiment, a combination of the aforementioned methods is employed. Regardless of the method, the temperature of the bed, or beds as the case may be, is raised to a particular target temperature effecting release (desorption) of the adsorbed gas ("sorbate"), in this instance water. To facilitate removal of the desorbing gas while simultaneously providing convective heat transfer to the sorbent, a preheated gas flow is commenced, commonly referenced as a "sweep" or "purge" gas. The sweep or purge gas enters the bed at a temperature suitable for the desired thermal desorption to take effect. Regardless of the use of the sweep or purge gas, a pressure driven force is applied for the removal of the gases from the sorbent bed, which is effected by connecting an outlet of the sorbent bed to an inlet of a pressure control device, for example, a vacuum pump, or a low pressure side of a pump, blower, fan, turbine, or preferably compressor. The outlet of any of these pressure control devices permits gases removed from the sorbent bed to be recovered for further processing or conditioning. Use of the sweep (or purge) gas facilitates removal of desorbed gas into the pressure control device.

In view of the above, regeneration of the water sorbent of this invention involves heating the at least partially saturated sorbent while passing a sweep gas, hereinafter "first sweep gas", through the sorbent, which causes desorption of water from the sorbent. Suitable first sweep gases include argon, nitrogen, air, carbon dioxide, ethane, propane and butane, with ethane being preferred. When ethane is employed, the sweep gas output 41 from the water sorbent unit 29 comprises ethane and water, which is beneficially recycled into the feed to the ethane steam cracker 43.

Subsequently, the dried steam cracker product stream 31 is passed through an ethylene sorbent, which for the purposes of this invention is defined as any material capable of selectively adsorbing ethylene from the dry steam cracker product stream. As noted hereinabove, the steam cracker product stream comprises a mixture of gaseous products and unconverted reactants, which in addition to ethylene and ethane include methane, acetylene, propane, propylene, propadiene and C4 hydrocarbons. More specifically, the ethylene sorbent comprises any metal-organic framework compound (MOF) capable of selectively adsorbing ethylene from the aforementioned product mixture. For the purpose of this invention, a MOF is defined as an array of positively charged metal ions surrounded by a plurality of organic linker molecules (linkers). The metal ions form nodes binding the linkers into a repeating cage-like structure. Acceptable metals include but are not limited to copper, manganese, chromium, iron, vanadium, nickel, zinc, aluminum and magnesium. Acceptable linkers include but are not limited to benzene-1,3,5-tricarboxylate, 2,5-dihydroxyterephthalic acid, 2,6-naphthalenedicarboxylic acid, 1,3,5-tris(4-carboxyphenyl)benzene and 1,3,5-tris(4-carboxyphenyl)benzene. MOFs envisioned for this invention, namely, those capable of separating ethylene from methane, ethane, and higher C3-C4 hydrocarbons, include such suitable, non-limiting MOF species disclosed, for example, by J. E. Bachman, et. al., J. Am. Chem. Soc., 2017, 139 (43), pp 15363-15370; Y. He, et. al., APL Materials 2, 124102 (2014); E. D. Bloch, et. al., Science, 2012, 335, 1606; R. B. Eldridge, Ind. Eng. Chem. Res., 1993, 32, 2208; X. Cui, et. al., Science, Vol. 353, Issue 6295, pp. 141-144; L. Mei, et. al., Journal of the Taiwan Institute of Chemical Engineers 70 (2017) 74-78; T. Hahnel, et. al., Microporous and Mesoporous Materials 224 (2016) 392-399; Z. R. Herm, E. D. Bloch, J. R. Long, Chem. Mater. 2014, 26, 323-338; and Y. Zhang, et. al., Chem. Commun., 2015, 51, 2714. In one embodiment, the MOF sorbent is selected from the group consisting of Zn-SIFSIX, Fe-MOF74, UTSA-10a, Cu-MOF-1 and Fe-MIL-100. The MOF can be further modified with additional functionalities; for example, chemically grafted with amine, carbonate, or hydroxyl containing inorganic or organic chemical species.

As intended for industrial practice, the ethylene sorbent is supported on a substrate that offers structural strength, increased surface area, and low pressure drop for acceptable throughput. Suitable substrates include meshes, porous structured materials, and porous monolithic materials.

In a preferred embodiment, the sorbent is applied as a layer or coating to a high surface area mesh substrate, preferably, a Microlith® brand mesh substrate having an ultra-short-channel-length (Precision Combustion, Inc., North Haven, Conn.). The mesh substrate is configured as a reticulated net or screen, that is, a substantially two-dimensional lattice wherein a thickness dimension is substantially smaller than length and width dimensions, and wherein the lattice contains a regular or irregular array of short pores and channels. In terms of materials of construction, the mesh substrate is selected from the group consisting of metal, ceramic, cermet, and woven fiberglass meshes and cloths, and any combination thereof. The mesh is not limited by any method of manufacture; for example, meshes can be constructed via weaving or welding fibers, or by an expanded metal technique as disclosed in U.S. Pat. No. 6,156,444, incorporated herein by reference, or by 3-D printing, or by a lost polymer method.

In more specific embodiments, the mesh substrate is constructed from any material provided that the resulting structure is capable of withstanding the temperatures and chemical environment to which the mesh is exposed. Suitable non-limiting materials for the mesh substrate include iron-chromium alloys, iron-chromium-aluminum alloys, iron-chromium-nickel alloys, copper and copper alloys, aluminum and aluminum alloys, and structural or composite polymers including polypropylene, nylons, or fiberglass. Such meshes are available commercially, for example, from McMaster-Carr, Alpha Aesar and Petro Wire & Steel. In one embodiment, the metal mesh comprises a Microlith® brand metal mesh obtainable from Precision Combustion, Inc., of North Haven, Conn., USA.

Pertaining to ceramic meshes, the term "ceramic" refers to inorganic non-metallic solid materials with a prevalent covalent bond, including but not limited to metallic oxides, such as oxides of aluminum, silicon, magnesium, zirconium, titanium, niobium, and chromium, as well as zeolites and titanates. Reference is made to U.S. Pat. Nos. 6,328,936 and 7,141,092, detailing insulating layers of short channel ceramic mesh comprising woven silica, both patents incorporated herein by reference. Pertaining to cermet meshes, the term "cermet" refers to a composite material comprising a ceramic in combination with a metal, illustrative metallic and ceramic materials outlined above; the composite being typically conductive while also exhibiting a high resistance to temperature, corrosion, and abrasion in a manner similar to ceramic materials.

More specifically, the mesh substrate is configured with a plurality of channels or pores having a diameter ranging from about 0.25 millimeters (mm) to about 1.0 mm, with a void space greater than about 60 percent, preferably up to about 80 percent or more. A ratio of channel length to diameter is generally less than about 2:1, preferably less than about 1:1, and more preferably, less than about 0.5:1. Preferably, the mesh has a cell density ranging from about 100 to about 1,000 cells or flow paths per square centimeter.

As described in U.S. Pat. Nos. 5,051,241 and 6,156,444, incorporated herein by reference, Microlith® brand mesh technology offers a unique design combining an ultra-short-channel-length with low thermal mass in one monolith, which contrasts with prior art monoliths having substantially longer channel lengths as noted hereinabove. For the purposes of this invention, the term "ultra-short-channel-length" refers to a channel length in a range from about 25 microns (μm) (0.001 inch) to about 500 μm (0.02 inch). In contrast, the term "long channels" pertaining to prior art monoliths refers to channel lengths greater than about 5 mm (0.20 inch) upwards of 127 mm (5 inches).

The loading of the ethylene sorbent onto the mesh substrate is described in units of weight sorbent per unit volume of substrate; and this advantageously ranges in one embodiment from about 50 mg ethylene sorbent per cubic centimeter substrate (50 mg/cm$^3$) to about 1,500 mg/cm$^3$. In another embodiment, the loading ranges from about 100 mg/cm$^3$ to about 750 mg/cm$^3$. This description takes gross dimensions of the substrate into account. The thickness and uniformity of a coating of the ethylene sorbent on the substrate vary depending upon the specific substrate, sorbent, and coating method selected.

In one embodiment, the ethylene adsorption step is conducted in a single ethylene sorbent bed, or alternatively in a plurality of ethylene sorbent beds connected in parallel, wherein in adsorption mode the cooled and dried steam cracker product stream containing an initial concentration of ethylene is contacted with the one or more ethylene sorbent beds for a selected time during which an effluent stream exiting the sorbent bed(s) contains an acceptably reduced concentration of ethylene. In another embodiment, the sorbent step (d) is conducted in a plurality of sorbent beds connected in series. In this embodiment, the cooled and dried steam cracker product stream containing an initial concentration of ethylene is contacted with a first ethylene sorbent bed to produce a first effluent stream of reduced ethylene concentration; and then the first effluent stream is contacted with a second ethylene sorbent bed to produce a second effluent stream of further reduced ethylene concentration; and so on until the steam cracker product stream has passed through all of the sorbent beds in series. In one embodiment, each sorbent bed, disposed in parallel or in series, contains the same identical MOF sorbent. In another embodiment, a portion of the sorbent beds disposed in parallel or in series contains one MOF sorbent; whilst a remaining portion of the sorbent beds contains a different MOF sorbent. There is no particular limit on the number of sorbent beds and types of MOFs employed. Typically, the number of sorbent beds ranges from about 1 to about 4. In another embodiment, use of the water removal sorbent unit 29 in FIG. 2 can be bypassed provided that a suitable water-resistant MOF sorbent composition is employed.

The ethylene adsorption step is conducted under any adsorption conditions providing for acceptable reduction of ethylene concentration from the dried steam cracker product stream. The conditions can vary depending upon the MOF species employed. Typically, the ethylene adsorption step is conducted at ambient temperature, suitably defined for this purpose as ranging from about 10° C. to about 25° C., and ambient pressure, suitably defined as about 1 bar (+/−10 percent). By-product stream 39 can be handled in a variety of ways. In one embodiment, a portion or all of by-product stream 39 is recycled into the ethane steam cracker unit 43. In another embodiment, a portion or all of by-product stream 39 is sent to one or more recovery units that function to recover hydrogen, propane, propylene, and/or other C3 products. In yet another embodiment, a portion or all of by-product stream 39 is vented or flared.

When at least one of the ethylene sorbent beds is fully or partially saturated with ethylene and the effluent stream exiting the one or more sorbent beds (33, 37) contains a detectable and, preferably, unacceptable concentration of ethylene (a condition known as "break-through"), the flow of dried steam cracker product stream 31 is stopped and the sorbent (or sorbents as the case may be) is regenerated via thermal desorption with collection of a purified ethylene product stream. The discussion presented hereinabove regarding regeneration of the water sorbent applies analogously to regeneration of the ethylene sorbent. Accordingly, regeneration of the at least partially saturated ethylene sorbent involves contacting a sweep gas ("second sweep gas") consisting of heated ethylene with the at least partially saturated ethylene sorbent under desorption conditions sufficient to provide the regenerated ethylene sorbent and a purified ethylene product stream comprising the sweep ethylene and the ethylene removed from the sorbent. The sweep ethylene is simply sourced from a tank of essentially pure ethylene as obtained, for example, from the overall process of this invention. The ethylene sorbent regeneration step is typically conducted at a temperature ranging from about 35° C. to about 100° C. and a pressure of about 1 bar (+/−10 percent).

Accordingly, the sweep ethylene is preheated by passing it through an ethylene compressor, making use of heat of compression; and then passing the compressed sweep ethylene into a cold side of a sweep gas heat exchanger so as to provide for additional heating, thereby resulting in the preheated ethylene sweep gas. The purified ethylene stream, exiting the ethylene sorbent under desorption conditions, is passed through a hot side of the sweep gas heat exchanger as a means of preheating the sweep ethylene gas. The purified ethylene product stream, which consists essentially of the sweep ethylene and the desorbed ethylene, requires no further separation, concentration, or purification, and as such is transferred to a bank of ethylene storage tanks for downstream use.

EMBODIMENTS

Example (E-1)

A computational model of the processes presented in FIG. 1 and FIG. 2 was built using commercially available thermodynamic-based chemical process modeling software, specifically, ChemCad purchased from Chemstations, Inc. of Houston, Tex.

The modeling parameters for the process of this invention are tabulated in Table 1, with the results of energy consumption presented in Table 2.

For comparative purposes, the energy consumption of the conventional present day process of producing ethylene, employing a plurality of fractionation columns for separations purposes, is taken from known values (E. Worrell, D. Phylipsen, D. Einstein, N. Martin, Lawrence Livermore Berkeley Laboratory (LLBL), DE-AC03-76SF00098, April, 2000), and presented in Table 2 as comparative experiment CE-1.

TABLE 1

Process of Invention - Modeling Parameters and Calculated Results

| Process Conditions | Water Removal (13X Mol. Sieve) | Ethylene Removal Stage 1 MOF | Ethylene Removal Stage 2 MOF |
|---|---|---|---|
| Inlet T (° C.) | 2 | 2 | 2 |
| Inlet P (bar) | 1.200 | 1.197 | 1.194 |
| H2O Partial Pressure (bar) | 0.00706 | | |
| H2O (g/s) | 0.056 | | |
| H2O removal (g) | 50.47 | | |
| Inlet C2H4 (g/s) | | 11.574 | 5.787 |
| Inlet CH4 (g/s) | | 0.509 | 1.018 |
| Target capture fraction C2H4 | | 0.500 | 1.000 |
| C2H4 removed (g) | | 5208.3 | 5208.3 |
| Sorbent capacity (g/g) | 0.21 | 0.0524 | 0.0584 |
| Capacity target (fraction) | 0.6 | 0.96 | 0.96 |
| Sorbent (g) | 400.6 | 103537.2 | 92899.8 |
| Sorbent loading (mg/in2) | 40 | 40 | 40 |
| Mesh area (cm2) | 64608.4 | 18699509 | 14983806 |
| Total Flow (mol/s) | 0.521 | 0.518 | 0.312 |
| CH4 capacity (g/g) | | 0.0000 | 0.0000 |
| CH4 captured | | 0.0 | 0.0 |
| Radial Flow Adsorber Unit | | | |
| ID (cm) | 10 | 10 | 10 |
| Length (cm) | 100 | 100 | 100 |
| Number of tubes | 1 | 10 | 1 |
| Inlet Area (cm2) | 3141.6 | 31415.9 | 31415.9 |
| Number of layers | 21 | 532 | 477 |
| Total Flow (mol/s) | 0.521 | 0.518 | 0.312 |
| Inlet Velocity (cm/s) | 3.720 | 0.377 | 1.607 |
| Pressure drop (bar) | 0.00156 | 0.00146 | 0.00891 |
| Temperature rise (° C.) | 0 | 0 | 0 |

TABLE 2

Energy Consumption (GJ/metric tonne C2H4)

| | *CONVENTIONAL Fractional Distillation (CE-1) | Process with MOF Sorbent (E-1) | Optimized Process with MOF Sorbent (E-1) |
|---|---|---|---|
| C2H4 Production Method | 4.8 | 4.8 | 4.8 |
| Compression | 3.5 | n/a | n/a |
| Purification | 4.2 | 3.0 | 1.6 |
| Total | 12.5 | 7.8 | 6.4 |
| Purification Energy Reduction (%) | — | 61.5 | 79.8 |
| Overall Energy Reduction (%) | — | 37.9 | 49.2 |

*E. Worrell, D. Phylipsen, D. Einstein, N. Martin, Lawrence Livermore Berkeley Laboratory LLBLDE-AC03-76SF00098, Apr., 2000.

When the comparative data (CE-1) of Table 2 are compared with the data of the example of this invention (E-1), it is apparent that the invention provides for an energy savings of from 38 percent to 49 percent over the conventional process of producing ethylene.

The results of Table 2 demonstrate the technical advantages of the claimed process in that a substantial energy savings is obtained from the claimed process and apparatus of preparing ethylene as compared with the present day conventional process. As well, the claimed process involves a more compact and simpler apparatus as compared to the fractionation system required of the conventional process.

As a further technical advantage the ethylene separation method of this invention by itself is applicable to separating ethylene from any chemical product stream comprising ethylene, including but not limited to streams derived from oxidative coupling of methane, non-oxidative coupling of methane, oxidative dehydrogenation of ethane, or non-oxidative dehydrogenation of ethane. The method of this invention can be equally applied to separations of propylene, butene, and in general other alkenes, and other paraffinic, isoparaffinic, aromatic or oxygenated hydrocarbons of value.

While the invention has been described in detail in connection with only a limited number of embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A process of producing ethylene comprising:
   (a) contacting an ethane feedstream and steam in a steam cracker under process conditions sufficient to prepare a steam cracker product stream comprising ethylene, unreacted ethane, water, and condensable hydrocarbons;
   (b) cooling the steam cracker product stream under conditions sufficient to obtain a cooled steam cracker product stream substantially free of water and liquid hydrocarbon condensates;
   (c) contacting the cooled steam cracker product stream with an ethylene sorbent comprising a substrate having supported thereon a metal-organic framework compound capable of selectively adsorbing ethylene, under adsorption conditions sufficient to remove the ethylene from the cooled stream cracker product stream;
   (d) when the ethylene sorbent is at least partially saturated with ethylene, stopping the flow of the cooled steam cracker product stream; and contacting the at least partially saturated ethylene sorbent with a flow of sweep ethylene under desorption conditions sufficient to regenerate the ethylene sorbent and recover a purified ethylene product stream comprising the sweep ethylene and desorbed ethylene.

2. The process of claim 1 wherein the steam cracker product stream is cooled in step (b) by means of heat exchange to a temperature between 1° C. and 10° C.

3. The process of claim 2 wherein step (b) comprises (b)(i) cooling the steam cracker product stream obtained from a steam cracker to a temperature between about 20° C. and about 60° C.; (b)(ii) passing a resulting steam cracker product stream through a compressor; (b)(iii) passing a resulting compressed steam cracker product stream into a hot side of a heat exchanger; and (b)(iv) passing a heat-exchanged steam cracker product stream through an expander so as to produce a cooled steam cracker product stream substantially free of bulk water and liquid hydrocarbon condensates and having a temperature between 1° C. and 10° C.

4. The process of claim 1 wherein prior to being fed to ethylene separation step (c), the cooled steam cracker product stream of step (b) is contacted with a water sorbent selected from the group consisting of aluminas, aluminosilicates, silicas, zeolites and molecular sieves so as to produce a cooled and dried steam cracker product stream.

5. The process of claim 4 wherein a cooled ethylene product stream is contacted with the water sorbent at a temperature between 1° C. and 10° C. and a pressure between 0.9 bar to 1.1 bar.

6. The process of claim 5 wherein after contact with the water sorbent, the cooled and dried steam cracker product stream has a water content of less than 1 percent by volume.

7. The process of claim 4 wherein when the water sorbent is at least partially saturated, the water sorbent is regenerated with a first sweep gas comprising ethane under conditions to regenerate the sorbent and produce a first sweep gas product stream comprising ethane and water, which stream optionally is recycled as a feed to the steam cracker.

8. The process of claim 1 wherein the metal-organic framework compound is selected from the group consisting of Zn-SIFSIX, Fe-MOF74, UTSA-10a, Cu-MOF-1 and Fe-MIL-100.

9. The process of claim 8 wherein the substrate of step (c) comprises a mesh having an ultra-short-channel-length ranging from 25 microns to 500 microns, and optionally, from 100 to 1,000 cells per square centimeter.

10. The process of claim 8 wherein a cooled ethylene product stream is contacted in step (c) with the ethylene sorbent at a temperature between 10° C. and 25° C. and a pressure of 1 bar (+/−10 percent).

11. The process of claim 1 wherein the at least partially saturated ethylene sorbent is contacted in step (d) with the sweep ethylene at a temperature ranging from 35° C. to 100° C. and a pressure of 1 bar (+/−10 percent).

12. An apparatus system for producing ethylene comprising:
   (a) a steam cracker configured to convert a mixture of ethane and steam into a steam cracker product stream;
   (b) a cooling module fluidly coupled to the steam cracker and configured with a cooling module inlet configured to receive the steam cracker product stream and further configured with a cooling module outlet configured to output a cooled steam cracker product stream substantially free of water and liquid hydrocarbon condensates;
   (c) at least one ethylene adsorption unit fluidly coupled to the cooling module and having disposed therein an ethylene sorbent comprising a substrate having supported thereon a metal-organic framework compound capable of selectively adsorbing ethylene;
   the at least one ethylene adsorption unit (c) further configured for an adsorption cycle with (c)(i) an adsorption cycle inlet configured to receive the cooled steam cracker product stream and to contact said cooled steam cracker product stream with the ethylene sorbent so as to remove ethylene, and (c)(ii) an adsorption cycle outlet configured to output a steam cracker product stream substantially free of ethylene;
   the at least one ethylene adsorption unit (c) further configured for a desorption cycle with (c)(iii) a desorption cycle inlet configured to receive an ethylene sweep stream and to contact said ethylene sweep stream with an at least partially saturated ethylene sorbent; and (c)(iv) a desorption cycle outlet configured to output a purified ethylene product stream comprising the sweep ethylene and desorbed ethylene.

13. The apparatus system of claim 12 wherein a water adsorption unit is coupled on an inlet end to (b) the cooling module and coupled on an outlet end to (c) the ethylene adsorption unit; the water adsorption unit having disposed therein a water sorbent, and further configured with (i) a water adsorption cycle inlet configured to receive the cooled steam cracker product stream substantially free of water and liquid hydrocarbon condensates, and with (ii) a water adsorption cycle outlet configured to output a cooled and dried stream cracker product stream.

14. The apparatus system of claim 13 wherein the water adsorption unit is further configured for a water desorption cycle with (iii) a water desorption cycle inlet configured to receive a first sweep gas and to contact same with an at least partially saturated water sorbent, and further configured with (iv) a water desorption cycle outlet configured to exhaust a first sweep gas product stream containing water.

15. The apparatus system of claim 14 wherein the first sweep gas comprises ethane, and the first sweep gas product stream containing ethane and water is coupled to a feed to the steam cracker.

16. A method of separating a chemical product stream comprising ethylene, the method comprising:
(a) contacting a chemical product stream comprising ethylene with an ethylene sorbent comprising a substrate having supported thereon a metal-organic framework compound capable of selectively adsorbing ethylene, under adsorption conditions sufficient to remove the ethylene and produce a chemical product stream substantially free of ethylene; and thereafter
(b) when the ethylene sorbent is at least partially saturated with ethylene, stopping the flow of the chemical product stream comprising ethylene, and contacting the ethylene sorbent with a flow of sweep ethylene under desorption conditions sufficient to produce a purified ethylene product stream comprising sweep ethylene and desorbed ethylene.

17. The method of claim 16 wherein the metal-organic framework compound is selected from the group consisting of Zn-SIFSIX, Fe-MOF74, UTSA-10a, Cu-MOF-1 and Fe-MIL-100.

18. The method of claim 16 wherein the substrate comprises a mesh having an ultra-short-channel-length ranging from 25 microns to 500 microns, and optionally from 100 to 1,000 cells per square centimeter.

19. The method of claim 16 wherein the at least partially saturated ethylene sorbent is contacted with the sweep ethylene at a temperature ranging from 35° C. to 100° C. and a pressure of 1 bar (+/−10 percent).

20. A process of regenerating an ethylene sorbent comprising contacting a flow of sweep ethylene with an ethylene sorbent comprising a substrate having supported thereon a metal-organic framework compound, the ethylene sorbent being at least partially saturated with adsorbed ethylene, the contacting occurring under desorption conditions sufficient to regenerate the ethylene sorbent and to produce a purified ethylene product stream comprising the sweep ethylene and desorbed ethylene.

* * * * *